(12) United States Patent
Arndt et al.

(10) Patent No.: US 7,446,870 B2
(45) Date of Patent: Nov. 4, 2008

(54) METHOD FOR VERIFICATION OF PARTICLES HAVING A SENSOR AREA AND SENSOR ARRANGEMENT FOR CARRYING OUT THIS METHOD

(75) Inventors: Frank Arndt, Berlin (DE); Jan Grahmann, Berlin (DE); Jens-Christian Holst, Berlin (DE); Jens Dahl Jensen, Berlin (DE); Ursus Krüger, Berlin (DE); Hendrik Rönsch, Berlin (DE); Arno Steckenborn, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 36 days.

(21) Appl. No.: 11/527,444

(22) Filed: Sep. 27, 2006

(65) Prior Publication Data
US 2007/0076207 A1 Apr. 5, 2007

(30) Foreign Application Priority Data
Sep. 30, 2005 (DE) .................. 10 2005 047 902

(51) Int. Cl.
*G01N 15/02* (2006.01)
(52) U.S. Cl. .................................... 356/335
(58) Field of Classification Search ......... None
See application file for complete search history.

(56) References Cited

U.S. PATENT DOCUMENTS

| | | | |
|---|---|---|---|
| 5,151,110 A | | 9/1992 | Bein et al. |
| 5,910,286 A | * | 6/1999 | Lipskier ............... 422/68.1 |
| 6,623,977 B1 | * | 9/2003 | Farquharson et al. ....... 436/164 |
| 7,208,077 B1 | * | 4/2007 | Albers et al. ............ 205/782 |
| 2002/0014415 A1 | | 2/2002 | Nakayama et al. |
| 2005/0016276 A1 | | 1/2005 | Guan et al. |
| 2005/0247559 A1 | | 11/2005 | Frey et al. |

FOREIGN PATENT DOCUMENTS

| | | |
|---|---|---|
| EP | 0 982 588 A1 | 3/2000 |
| EP | 982 588 A1 | 3/2000 |
| WO | WO 2004/001405 | 12/2003 |

* cited by examiner

*Primary Examiner*—Michael P Stafira
(74) *Attorney, Agent, or Firm*—Young & Thompson

(57) ABSTRACT

The invention relates to a method for verification of particles, in particular of nanoparticles (16), in which a sensor area (15) is made available for this purpose, on which the particles can accumulate. The invention also relates to a sensor arrangement having a sensor area (15) which is suitable for carrying out the method mentioned. The invention provides for a plurality of sensor areas (15) to be arranged, on which particles which each have different characteristics can accumulate. For example, this makes it possible to classify nanoparticles (16) of different size, thus advantageously allowing a statement to be made on the size distribution of the nanoparticles (16) in a nanopowder.

17 Claims, 2 Drawing Sheets

Figure 1:
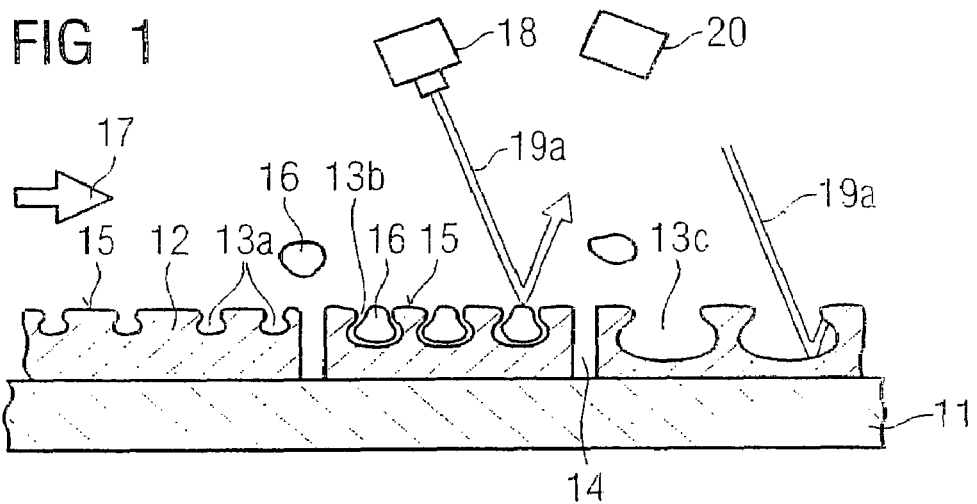

METHOD FOR VERIFICATION OF PARTICLES HAVING A SENSOR AREA AND SENSOR ARRANGEMENT FOR CARRYING OUT THIS METHOD

The invention relates to a method for verification of particles, in which a sensor area is made available, on which the particles to be verified accumulate when they are present, and in which the characteristics of the sensor area are monitored with respect to one parameter which varies on the basis of the accumulation of the particles.

A method of the type mentioned in the introduction is described, for example, in EP 982 588 A1 and is used for smoke detection. The smoke to be verified comprises nanoparticles which can be verified as particles in the air. For this purpose, a sensor area is provided in a housing, and its surface has a molecular imprinted structure. This surface may be formed, for example, by a polymer, in which case polymers such as these are also referred to as so-called MIP (molecular imprinted polymers). The surface formed in this way is produced by the particles to be verified, for example smoke gas particles, being embedded in the polymer matrix during the formation of the polymer layer, and being dissolved from this matrix after it has been cured. The resultant pores are selectively suitable for absorption of the same type of smoke gas particles as those embedded during the production, so that, if smoke occurs once again, smoke gas particles are introduced into the relevant layer.

The sensor area is in the form of a system which can oscillate in the fire alarm according to EP 982 588 A1, so that, in principle, a resonant frequency of this system which can oscillate is changed by the introduction of the smoke gas particles. By way of example, a surface acoustic wave generator can be applied to the surface of the system which can oscillate, as the system which can oscillate. This surface acoustic wave generator comprises electrodes which are applied to the surface, which produce waves which propagate on the surface of the system which can oscillate. Depending on the load state of the coating, these waves (also referred to as surface acoustic waves, SAW) propagate at a different speed. The speed of propagation can be determined by means of an electrode pair arranged opposite the transmitting electrode pair. The surface acoustic wave generator with the detector electrode pair thus forms a monitoring apparatus for the sensor area, by means of which it is possible to measure the change in one parameter, specifically the natural frequency of the system which can oscillate, resulting from the accumulation of particles on the surface.

Detectors of the type mentioned in the introduction are also used for detection of gas molecules. In this case, these form the particles to be verified. In this case, by way of example, polymer layers are used as the coating, on which specific gas molecules can accumulate. In this case, the increase in mass is less than in the case of the accumulation of nanoparticles, but can nevertheless be verified by suitable systems which can oscillate.

The object of the invention is to specify a method for verification of particles, by means of which it is possible to make comparatively versatile statements relating to the particles to be verified.

This object is achieved according to the invention by the method specified in the introduction, in that a plurality of sensor areas are made available, and are sensitive to particles with different characteristics. This advantageously means that the sensor areas can react specifically to different characteristics of the particles, since they intrinsically bind the particles having the respective specific characteristics, and can thus register these characteristics by monitoring the sensor areas. By way of example, the characteristics may relate to the composition of the particles or their surface structure, in which case the sensor areas react to the characteristics to be verified. The use of a plurality of sensor areas has the advantage that a medium with the particles to be verified (for example nanoparticles such as smoke or molecules, for example a poisonous gas) can be investigated for a plurality of characteristics in a single investigation step. This results in a saving in analysis time, thus improving the economy of the verification process and allowing the rapid reaction to the verification of specific characteristics of the particles.

One refinement of the invention provides for the sensor areas to be monitored in parallel. This makes it possible to determine an accumulation of particles on the sensor areas immediately after this event starts. Furthermore, the concentration of the particles in the medium can be deduced from the rate of change of the oscillation characteristics. In particular, the medium for the particles may be a gas or a liquid, in which case the medium may also be formed by the particles themselves.

Another refinement of the method provides that the characteristics of the particles to be verified differ in terms of their chemical nature or in terms of their composition. In this case, when carrying out the method, the reaction must be in such a form that the sensor areas are sensitive to different chemical characteristics and/or their composition, so that carrying out the method also results in the desired result. This allows, for example, specific substance classes to be verified which have specific functional groups (for example specific oligonucleotides or else inorganic groups in the molecules which give specific characteristics to a substance class, such as alcohols, acids, etc.).

According to yet another refinement of the invention, the particles to be verified are nanoparticles whose sizes differ from one another. In this case, it is desirable to know the size distribution of the nanoparticles, which is achieved by the specificity of the sensor areas to specific size classes of the nanoparticles. At the same time, the concentration of the corresponding size class of nanoparticles in the total volume of the amount of nanoparticles investigated can be determined as a function of the change in the oscillation behavior with respect to the load level. This advantageously allows nanoparticular raw materials to be classified.

It is advantageous for the sensor areas for classification of the nanoparticles to be formed by molecular imprinted surfaces. The already mentioned MIP can be used for this purpose. In this case, the MIPs are produced using the nanoparticles to be investigated, which homogeneously have the size class to be verified. In this case, the expression a size class means a size range of the nanoparticles, in which case, by way of example, the size is related to the mean diameter of these nanoparticles.

The invention furthermore relates to a sensor arrangement having a sensor area on which particles to be verified accumulate when they are present, and having a monitoring apparatus for the sensor area, by means of which it is possible to determine a change in one parameter of the sensor area on the basis of the accumulation of the particles.

One example of said sensor arrangement is described in the already mentioned EP 982 588 A1. Against this background, a further object is to specify a sensor arrangement having a sensor area for the particles to be verified, which allows universal and economic use.

This object is achieved by said sensor arrangement according to the invention in that a plurality of sensor areas are provided, and are sensitive to particles with different characteristics. This makes it possible to achieve the advantages which have already been explained with respect to the method according to the invention, specifically that parallel investigation of particles with different characteristics is possible, in which case a plurality of these characteristics can be determined at the same time. In particular, this makes it possible to investigate particle mixtures in a short time, thus justifying the economy of the sensor arrangement according to the invention.

One refinement of the sensor arrangement provides for the sensor areas to be arranged alongside one another in an array. This advantageously makes it easier to manufacture the sensor arrangement. Furthermore, the arrangement of the sensor areas alongside one another means that the medium to be investigated can be applied to the sensor formed in this way in a particularly simple and uniform manner.

A further refinement of the invention provides for the sensor areas to be sensitive to nanoparticles in different size ranges. This makes it possible to achieve the already mentioned advantages, that the sensor areas can be used to classify nanoparticles on the basis of their size distribution.

It is also advantageous if the size ranges which are predetermined by the sensitivity of the sensor areas overlap. This allows more differentiated analysis of the medium containing the nanoparticles. This is because higher resolution can be achieved for evaluation of the size ranges, if, for example, one size class of nanoparticles is deposited on sensor areas with adjacent size ranges. If the possible size classes are sufficiently well known in the medium to be investigated, it is possible to draw conclusions about the concentration of the nanoparticles which are located in the overlapping area of the size classes. An additional sensor area would be required for this purpose if the size ranges did not overlap, covering precisely this size range of the overlap of two adjacent size ranges.

According to one particular refinement of the sensor arrangement, the sensor areas are formed in a micromechanical manner in the surface of a substrate, with the sensor areas being separated from one another by cutouts in this surface. This allows the verification system to be miniaturized which, in addition to the advantages of a smaller physical size, also allows, in particular, the advantage of greater verification sensitivity of the sensor areas. This is because micromechanically produced sensor areas are far more sensitive to very small amounts of accumulated particles to be verified because their own mass is low. The production of the sensor areas by means of cutouts in the surface also advantageously allows the use of production methods which are familiar from micromechanics, such as etching.

By way of example, the monitoring apparatus may advantageously comprise an electromagnetic transmitter, which is directed at the sensor area, and a receiver for radiation from the electromagnetic transmitter which has been reflected from the sensor area. In this case, the reading principle makes use of the fact that the surface of the sensor area on which the particles are located has different optical characteristics than when there are no particles there. The reading process takes place in a similar manner to the principle of a CD-ROM drive, in which the data is produced by a change in the optical characteristics of the data storage medium. This provides a reading method which can advantageously make use of a proven technique.

Another advantageous option for the provision of a monitoring apparatus provides for this monitoring apparatus to contain a bearing, which can oscillate, for the sensor areas, an actuator for oscillation excitation of the sensor areas, and a measurement device for the oscillation frequency and/or amplitude of the oscillations. The bearing, which can oscillate, of the sensor area also, of course, in fact comprises not only the area itself but also the mounting body which forms the area. When formed micromechanically, this may, for example, be an underetched area of the silicon substrate which is additionally provided with the layer that creates the sensor area. Accumulation of particles to be verified on the sensor area then results in a change in the oscillation behavior of an oscillator that is produced in this way. This change can be determined when the oscillator is excited. This change comprises a discrepancy from the design-dependent oscillation frequency of the oscillator which is formed, and this frequency can be measured directly. If the oscillator is excited with a known amount of energy being introduced into it, the measurement of the amplitude may also, however, allow conclusions to be drawn about the change in the oscillation frequency of the oscillator, since the amplitude of the oscillator is dependent on the discrepancy between the oscillation excitation and the resonant frequency.

Figure 2:
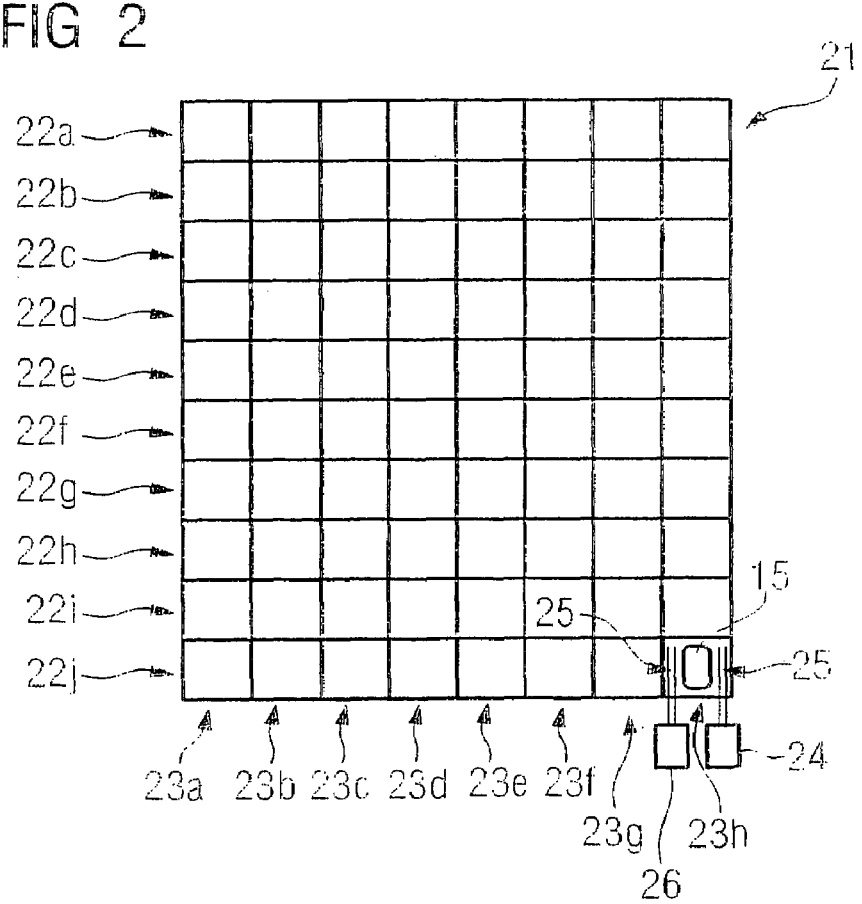
Figure 3:
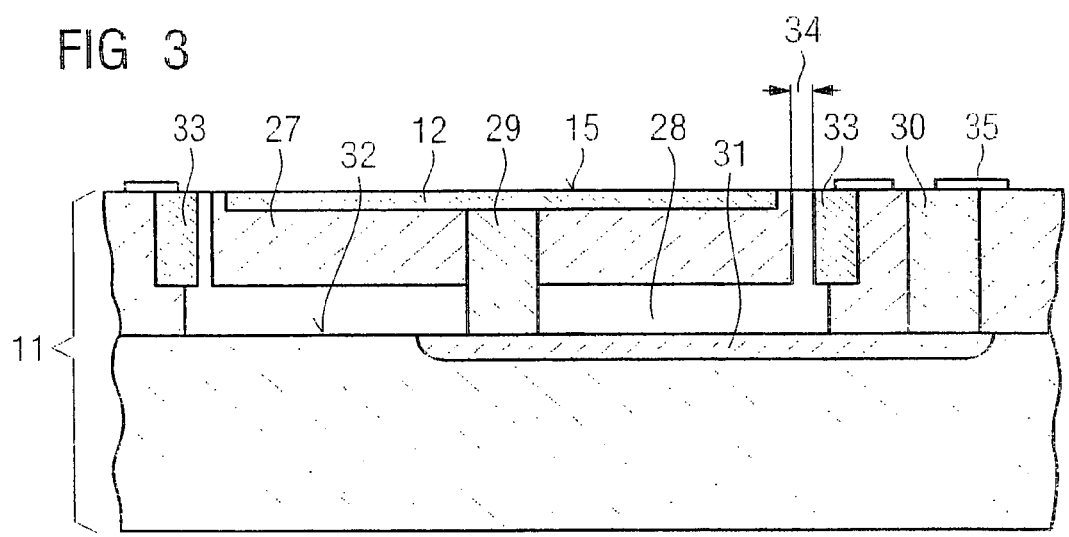

Further details of the invention will be described in the following text with reference to the drawing. Identical or corresponding drawing elements in the figures are each provided with the same reference symbols and will be explained more than once only where there are differences between the individual figures. In the figures:

FIG. 1 shows a schematic cross section through an array of sensor areas based on one exemplary embodiment of the sensor arrangement according to the invention, FIG. 2 shows a schematic view of an array of sensor areas based on another exemplary embodiment of the sensor arrangement according to the invention, and FIG. 3 shows a sensor area of a sensor array based on a further exemplary embodiment of the sensor arrangement according to the invention, in the form of a section.

A sensor arrangement as shown in FIG. 1 has a substrate 11 on which a coating 12 with pores 13a, 13b, 13c is applied. The coating is subdivided by grooves into a series of sensor areas 15. The pores 13a, 13b, 13c each have a different size class per sensor area.

The sensor arrangement may, for example, be inserted into a chamber (not illustrated) which allows nanoparticles 16 to be supplied. These migrate along the sensor areas, corresponding to the arrow 17 that is indicated, and are deposited selectively on the sensor area with the pores 13b, on the basis of the advantageous behavior of the adhesion forces, since the size of these pores is suitable for the nanoparticles being investigated in the exemplary embodiment. The other sensor areas with the pores 13a and 13c in contrast have no nanoparticles on them.

Subsequent evaluation by means of a laser beam 19a, which originates from a transmitter 18, results in a significantly different reflection behavior of the sensor area 15 whose pores 13b have nanoparticles 16 on them. This reflection behavior can be registered by means of a receiver, for example a photodiode, which is suitable for the laser beam 19a, so that it is possible to deduce the investigated particle size.

FIG. 1 also indicates that sensor areas with no nanoparticles have a different reflection behavior. A laser beam 19b, which can be transmitted from the same transmitter 18, is not reflected, or is scarcely reflected, in the depicted manner by the sensor area with the pores 13c, since it is absorbed in one of the pores 13c.

The sensor apparatus as illustrated in FIG. 1 may, of course, also be used to investigate mixtures of nanoparticles of different size classes, in which case there will be nanoparticles on a plurality of the sensor areas. The degree of coverage of the sensor areas can also be used to reduce the concentration ratio of the nanoparticles in different size classes.

FIG. 2 illustrates schematically how the sensor areas 15 are arranged in an array 21. The array shown in FIG. 2 is two-dimensional, although it could likewise also be one-dimensional, that is to say in the form of a single row. The array 21 shown in FIG. 2 has rows 22a to 22j, in which the sensor areas are each specific for nanoparticles of different size classes. The size classes may, for example, cover the entire size spectrum that is relevant for nanoparticles, from less than one nanometer to 1000 nanometers. By way of example, the ten rows 22a to 22j may each be graduated in uniform steps of 100 nanometers. Another option is an association with size classes which, in relative terms always cover an identical range, that is to say the row 22a from 0.5 to 1 nanometer, the row 22b from 1 to 2 nanometers, the row 22c from 2 to 4 nanometers, etc. It is also possible for the respective size classes to overlap, for example row 22a from 1 to 5 nanometers, row 22b from 3 to 9 nanometers, row 22c from 7 to 15 nanometers, etc.

The columns 23a to 23h of the array 21 are available for production of specifics relating to the size of the nanoparticles with independent characteristics. By way of example, these may be chemical characteristics, in which case the specifics for nanoparticles with specific chemical characteristics may be achieved, for example, by the use of MIP. The molecular imprinted pores are then subdivided on a row-dependent basis into specific size classes, in which case only nanoparticles whose chemical structure "fits" the pores can accumulate, by virtue of the chemical structures in the pores.

Furthermore, individual columns, for example the column 23h, can also be provided for gas molecules which, by way of example, can be mixed as reactive components with a mixture of nanoparticles. The number of gas molecules such as these on a sensor area can be used to deduce the concentration of the gas in the nanoparticle mixture. However, there is no point in distinguishing on the basis of particle size in the case of molecules.

By way of example, in the sensor field in row 22j and column 23h, one of the sensor fields 15 is illustrated, in which there is also a verification apparatus, comprising a generator 26 and a detector 24 for surface acoustic waves. The generator 26 and the detector 24 have suitable electrodes 25, which are fitted to the surface of the array on both sides of the sensor field 15, in order to produce and to register the surface acoustic waves.

FIG. 3 illustrates a detail of an array in which the sensor area 15 is formed by a plate resonator 27. The plate resonator 27 has a coating 12 on which, by way of example, gas molecules to be verified have accumulated (not illustrated). The plate resonator 27 is accommodated in a depression 28 which is formed using etching technology in the substrate 11, which is formed from a layer assembly. The plate resonator 27 is mounted on a pillar-like suspension means 29 in the depression 28, so that the areas which extend to the edge of the plate resonator 27 can oscillate freely.

The pillar-like suspension means 15 at the same time forms one electrode, with which electrical contact can be made through a via 30 in the upper layer of the substrate 11 and a conductive path 31 in the lower layer of the substrate 11, which at the same time forms the bottom 32 of the depression. Further electrodes 33 are integrated in the edge of the depression 28 and are adjacent to the side edges of the plate resonator 27, forming a gap 34. In order to excite the plate resonator 27 to oscillate, the electrodes 33 as well as the pillar-like suspension means 29 can be connected to an AC voltage source via interconnects 35, which run on the upper face of the substrate 11.

As soon as gas molecules accumulate on the surface 15 of the layer 12, the resonant frequency of the plate resonator 27 changes as a result of the change in its oscillating mass. By way of example, the shift in the resonant frequency can be measured by finding the new resonant frequency by modification of the excitation. Another possibility is to determine the magnitude of the damping which results from the shift in the resonant frequency. The damping and/or the shift in the resonant frequency can also be used to deduce the increase in the oscillating mass of the plate resonator 27, and thus the mass of the accumulated particles. The interconnects 35 therefore also form the interface for determination of the detection results. The measurement device which is required for this purpose is not illustrated.

The invention claimed is:

1. A method for verification of nanoparticles (16), said method comprising:
    providing a plurality of sensor areas (15) on which the nanoparticles (16) to be verified accumulate when said nanoparticles (16) are present, and
    monitoring the characteristics of the plurality of sensor areas (15) with respect to one parameter which varies on the basis of the accumulation of the nanoparticles (16),
    wherein the plurality of sensor areas (15) are made available, and are sensitive to nanoparticles (16) of different sizes and the plurality of sensor areas have a specificity to specific size classes of nanoparticles.

2. The method as claimed in claim 1, wherein the plurality of sensor areas (15) are monitored in parallel.

3. The method as claimed claim 1, wherein the the plurality of sensor areas (15) are further sensitive to nanoparticles (16) of a different chemical nature or of a different composition.

4. The method as claimed in claim 1, wherein the plurality sensor areas (15) are formed by molecular imprinted surfaces.

5. A sensor arrangement comprising:
    a plurality of sensor areas (15) on which nanoparticles (16) to be verified accumulate when said nanoparticles (16) are present, and
    a monitoring apparatus (24, 25, 26) for the plurality of sensor areas (15), capable of determining a change in one parameter of at least one of the plurality of sensor areas (15) on the basis of the accumulation of the nanoparticles (16),
    wherein the plurality of sensor areas (l5) are sensitive to nanoparticles (16) of different size ranges.

6. The sensor arrangement as claimed in claim 5, wherein the plurality of sensor areas (15) are arranged alongside one another in an array (21).

7. The sensor arrangement as claimed in claim 5, wherein the size ranges which are predetermined by the sensitivity of the plurality of sensor areas (15) overlap.

8. The sensor arrangement as claimed in claim 6, wherein the plurality of sensor areas (15) are formed in a micromechanical manner in the surface of a substrate (11), with the plurality of sensor areas being separated from one another by cutouts (14, 34) in this surface.

9. The sensor arrangement as claimed in claim 6, wherein the monitoring apparatus comprises an electromagnetic transmitter (18), which is directed at the plurality of sensor areas, and a receiver (20) for radiation (19a, 19b) from the electromagnetic transmitter which has been reflected from the plurality of sensor areas (15).

10. The sensor arrangement as claimed in claim 6, wherein the monitoring apparatus contains a bearing (29), which can oscillate, for the plurality of sensor areas (15), an actuator (33) for oscillation excitation of the plurality of sensor areas, and a measurement device for the oscillation frequency and/or amplitude of the oscillations.

11. The sensor arrangement as claimed in claim 5, wherein the plurality of sensor areas (15) are formed in a micromechanical manner in the surface of a substrate (11), with the plurality of sensor areas being separated from one another by cutouts (14, 34) in this surface.

12. The sensor arrangement as claimed in claim 7, wherein the plurality of sensor areas (15) are formed in a micromechanical manner in the surface of a substrate (11), with the plurality of sensor areas being separated from one another by cutouts (14, 34) in this surface.

13. The sensor arrangement as claimed in claim 5, wherein the monitoring apparatus comprises an electromagnetic transmitter (18), which is directed at the plurality of sensor areas, and a receiver (20) for radiation (19*a*, 19*b*) from the electromagnetic transmitter which has been reflected from the plurality of sensor areas (15).

14. The sensor arrangement as claimed in claim 7, wherein the monitoring apparatus comprises an electromagnetic transmitter (18), which is directed at the plurality of sensor areas, and a receiver (20) for radiation (19*a*, 19*b*) from the electromagnetic transmitter which has been reflected from the plurality of sensor areas (15).

15. The sensor arrangement as claimed in claim 5, wherein the monitoring apparatus contains a bearing (29), which can oscillate, for the plurality of sensor areas (15), an actuator (33) for oscillation excitation of the plurality of sensor areas, and a measurement device for the oscillation frequency and/or amplitude of the oscillations.

16. The sensor arrangement as claimed in claim 7, wherein the monitoring apparatus contains a bearing (29), which can oscillate, for the plurality of sensor areas (15), an actuator (33) for oscillation excitation of the plurality of sensor areas, and a measurement device for the oscillation frequency and/or amplitude of the oscillations.

17. The sensor arrangement as claimed in claim 8, wherein the monitoring apparatus contains a bearing (29), which can oscillate, for the plurality of sensor areas (15), an actuator (33) for oscillation excitation of the plurality of sensor areas, and a measurement device for the oscillation frequency and/or amplitude of the oscillations.

* * * * *